United States Patent
Okoshi

(10) Patent No.: US 7,569,708 B2
(45) Date of Patent: Aug. 4, 2009

(54) LIQUID CYCLOHEXANE-TRICARBOXYLIC ACID ANHYDRIDE

(75) Inventor: Atsushi Okoshi, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 625 days.

(21) Appl. No.: 10/579,446

(22) PCT Filed: Nov. 19, 2004

(86) PCT No.: PCT/JP2004/017231

§ 371 (c)(1),
(2), (4) Date: May 16, 2006

(87) PCT Pub. No.: WO2005/049597

PCT Pub. Date: Jun. 2, 2005

(65) Prior Publication Data

US 2007/0123716 A1    May 31, 2007

(30) Foreign Application Priority Data

Nov. 20, 2003    (JP) .............................. 2003-390455

(51) Int. Cl.
*C07D 307/89* (2006.01)
(52) U.S. Cl. ..................................... 549/245
(58) Field of Classification Search ................ 549/245
See application file for complete search history.

(56) References Cited

U.S. PATENT DOCUMENTS 5,412,108 A    5/1995    Fisher

FOREIGN PATENT DOCUMENTS

| JP | 54-048739 | 4/1979 |
|----|-----------|--------|
| JP | 55-072184 | 5/1980 |
| JP | 55-115879 | 9/1980 |
| JP | 57-206678 | 12/1982 |
| JP | 08-325196 | 12/1996 |

*Primary Examiner*—Bernard Dentz
(74) *Attorney, Agent, or Firm*—Antonelli, Terry, Stout & Kraus, LLP.

(57) ABSTRACT

Trans, trans-1,2,4-cyclohexanetricarboxylic acid-1,2-anhydride represented by the following formula 1:

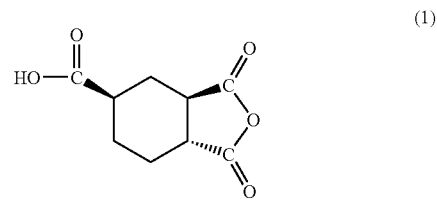

(1)

a cyclohexanetricarboxylic anhydride being liquid at ordinary temperatures which contains such a anhydride, and a production method thereof. The cyclohexanetricarboxylic anhydride being liquid at ordinary temperatures is produced by melting 1,2,4-cyclohexanetricarboxylic acid and/or 1,2,4-cyclohexanetricarboxylic acid-1,2-anhydride at 180 to 300° C. under heating. Since the cyclohexanetricarboxylic anhydride is liquid at ordinary temperatures, it is advantageously used in industrial applications such as raw materials or modifiers for coating compositions, adhesives, shaped articles, sealing resins for photosemiconductors, curing agents and polyimide resins, raw materials for plasticizers and lubricant oils, intermediates for medicines and agricultural chemicals, raw material for coating resins, raw material for toner resins, etc.

5 Claims, No Drawings

LIQUID CYCLOHEXANE-TRICARBOXYLIC ACID ANHYDRIDE

TECHNICAL FIELD

The present invention relates to a cyclohexanetricarboxylic anhydride being liquid at ordinary temperatures, which contains a compound having a novel structure. The liquid cyclohexanetricarboxylic anhydride is useful as raw materials or modifiers for coating compositions, adhesives, shaped articles, sealing resins for photosemiconductors, curing agents and polyimide resins, raw materials for plasticizers and lubricant oils, intermediates for medicines and agricultural chemicals, raw material for coating resins, raw material for toner resins, etc.

BACKGROUND ART

High luminance blue LED and white LED which have been recently developed have come to find wide applications in backlights for display boards, full color displays and cellular phones, etc. As the sealing materials for photoelectric transducers such as LED, a heat-curable resin composition containing an epoxy-containing compound and an acid anhydride curing agent has been conventionally used because of its excellent colorless transparency. As the curing agent for epoxy-containing compound used in sealing photoelectric transducers, alicyclic acid anhydrides such as methylhexahydrophthalic anhydride, methyltetrahydrophthalic anhydride, hexahydrophthalic anhydride and tetrahydrophthalic anhydride have been generally used. Among such anhydrides, methylhexahydrophthalic anhydride and methyltetrahydrophthalic anhydride which are liquid at ordinary temperatures have been mainly used because of their easiness of handling.

As the production method for the cyclohexanetricarboxylic anhydride, there have been proposed a method in which trimellitic acid is hydrogenated by molecular hydrogen in a polar solvent in the presence of a rhodium catalyst supported on activated carbon having a specific surface area of 940 m$^2$/g or more, and then, cis,cis-1,2,4-cyclohexanetricarboxylic acid which is obtained by recrystallization from tetrahydrofuran and/or acetonitrile solvent is converted into an anhydride by using an anhydrizing agent such as acetic anhydride (Patent Document 1), and a method in which an alkyl trimellitate is nuclear-hydrogenated into an alkyl 1,2,4-cyclohexanetricarboxylate under heating in the presence of a noble metal-containing hydrogenation catalyst and an aliphatic alcohol, the resultant ester is hydrolyzed in sulfolane and/or dimethyl sulfoxide solvent, and then the obtained 1,2,4-cyclohexanetricarboxylic acid is cyclized by anhydrization (Patent Document 2). However, the cyclohexanetricarboxylic anhydrides obtained in the proposed methods are all solid.

Since the cyclohexanetricarboxylic anhydride produced by known methods is solid and therefore hard to handle, such an anhydride is often used after being dissolved in a solvent. This makes the operation complicated and requires a drying step which can cause the pollution of environment in some cases.

It has been expected that the cyclohexanetricarboxylic anhydride will find many applications such as sealing resins for photosemiconductors because of its excellent colorless transparency. However, the solid nature of the known cyclohexanetricarboxylic anhydride makes its handling difficult to limit the application.

[Patent Document 1] U.S. Pat. No. 5,412,108

[Patent Document 2] JP 8-325196A

DISCLOSURE OF INVENTION

An object of the present invention is to provide an easy-to-handle and liquid cyclohexanetricarboxylic anhydride.

As a result of extensive research in view of achieving the object, the inventor has found that an anhydride being liquid at ordinary temperatures which contains a cyclohexanetricarboxylic anhydride having a novel structure is obtained by melting cyclohexanetricarboxylic acid and/or cyclohexanetricarboxylic anhydride under heating. The present invention is based on this finding.

Thus, the present invention provides a cyclohexanetricarboxylic anhydride having the following novel structure, a cyclohexanetricarboxylic anhydride which is liquid at ordinary temperatures, and a production method thereof.

(1) Trans, trans-1,2,4-cyclohexanetricarboxylic acid-1,2-anhydride represented by the following formula 1:

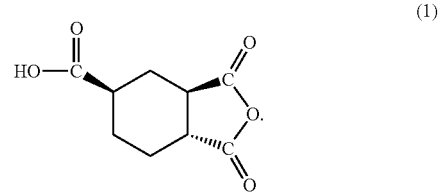

(2) A cyclohexanetricarboxylic anhydride being liquid at ordinary temperatures which contains trans, trans-1,2,4-cyclohexanetricarboxylic acid-1,2-anhydride described in item 1.

(3) The cyclohexanetricarboxylic anhydride being liquid at ordinary temperatures as described in item 2, which has a color number of 100 Hazen or less.

(4) A method of producing the cyclohexanetricarboxylic anhydride being liquid at ordinary temperatures as described in item 2, which includes a step of melting 1,2,4-cyclohexanetricarboxylic acid and/or 1,2,4-cyclohexanetricarboxylic acid-1,2-anhydride at 180 to 300° C. by heating.

(5) The method of producing the cyclohexanetricarboxylic anhydride being liquid at ordinary temperatures as described in item 4, which further includes a step of purifying the cyclohexanetricarboxylic anhydride by distillation after the step of melting by heating.

BEST MODE FOR CARRYING OUT THE INVENTION

The raw material for the cyclohexanetricarboxylic anhydride which is liquid at ordinary temperatures may include 1,2,4-cyclohexanetricarboxylic acids and/or solid 1,2,4-cyclohexanetricarboxylic acid-1,2-anhydrides.

The 1,2,4-cyclohexanetricarboxylic acids can be produced by a direct hydrogenation of benzenetricarboxylic acid, a hydrogenation of benzenetricarboxylic acid ester, a hydrogenation of alkali metal benzenetricarboxylate, etc. Any of 1,2,4-cyclohexanetricarboxylic acids produced by these method can be used as the raw material for the cyclohexanetricarboxylic anhydride which is liquid at ordinary temperatures.

The 1,2,4-cyclohexanetricarboxylic acid-1,2-anhydrides also usable as the raw material can be produced by an anhydrization of 1,2,4-cyclohexanetricarboxylic acids in the presence of an anhydrizing agent such as acetic anhydride.

As described in Patent Document 1, the 1,2,4-cyclohexanetricarboxylic acid-1,2-anhydride produced by the anhydrization using an anhydrizing agent such as acetic anhydride is solid cis, cis-1,2,4-cyclohexanetricarboxylic acid-1,2-anhydride having a melting point (mp) of 154 to 156° C. represented by the following formula 2:

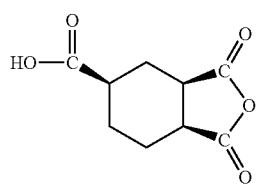

(2)

The cyclohexanetricarboxylic anhydride which is liquid at ordinary temperatures of the invention can be produced by a method including a step of melting the above raw material such as 1,2,4-cyclohexanetricarboxylic acids under heating. By the melting of the raw material under heating, anhydrization and isomerization occur when the 1,2,4-cyclohexanetricarboxylic acid is used as the raw material, whereas isomerization proceeds when the 1,2,4-cyclohexanetricarboxylic acid-1,2-anhydride is used as the raw material, to obtain a mixture of cyclohexanetricarboxylic anhydrides which is liquid at ordinary temperatures in each case.

The melting under heating is conducted under any pressure conditions of atmospheric pressure, reduced pressure and applied pressure, with atmospheric pressure and reduced pressure being preferred in view of easiness of removing the water which is generated with the progress of anhydrization. The melting under heating is also preferably conducted in an atmosphere of inert gas such as nitrogen gas, preferably in the inert gas flow in view of easiness of removing the generated water.

The melting under heating is sufficiently conducted at temperatures at which the raw material such as cyclohexanetricarboxylic acids and/or cyclohexanetricarboxylic acid anhydrides is melted. Since the rates of anhydrization and isomerization are low at lower temperatures and the side reaction such as decarboxylation is likely to occur, the melting under heating is conducted preferably at 180 to 300° C., and more preferably at 190 to 280° C.

The time for the melting under heating is preferably within 24 h and more preferably 0.1 to 10 h in view of the production efficiency, although depending upon the temperature.

The melting under heating may be carried out in either batchwise manner and continuous manner. By suitably changing the temperature and time for the melting under heating, the viscosity of the cyclohexanetricarboxylic anhydride which is liquid at ordinary temperatures can be regulated within a desired range.

By conducting the purification by distillation after the melting step under heating, a cyclohexanetricarboxylic anhydride being liquid at ordinary temperatures which is less colored can be produced. The color number thereof is 100 Hazen or less, and preferably 50 Hazen or less. The Hazen color number may be measured by a spectrocolorimeter, etc.

The distillation may be carried out in either batchwise manner or continuous manner. It is preferred to minimize the heat history to avoid the decomposition of the aimed product and the formation of high-boiling products. Any of a simple distillation and a multi-plate distillation may be employed.

The distillation pressure is preferably 15 mmHg (2 kPa) or less and more preferably 10 mmHg (1.3 kPa) or less, because the decomposition of the aimed product and the formation of high-boiling products can be avoided.

By the melting under heating mentioned above, a mixture of isomeric cyclohexanetricarboxylic anhydrides is obtained, which contains trans, trans-1,2,4-cyclohexanetricarboxylic acid-1,2-anhydride of the formula 1 and cis, cis-1,2,4-cyclohexanetricarboxylic acid-1,2-anhydride of the formula 2 which is disclosed in Patent Document 1.

Trans, trans-1,2,4-cyclohexanetricarboxylic acid-1,2-anhydride of the invention can be fractionated by HPLC and its stereostructure can be identified by NMR analysis, as will be described in the following examples.

The content of trans, trans-1,2,4-cyclohexanetricarboxylic acid-1,2-anhydride in the cyclohexanetricarboxylic anhydride which is liquid at ordinary temperatures is 1 to 100% by mass and preferably 5 to 95% by mass.

Trans, trans-1,2,4-cyclohexanetricarboxylic acid-1,2-anhydride may be isolated from the mixture by a purification method such as column adsorption, distillation and extraction.

Since the cyclohexanetricarboxylic anhydride of the invention is liquid at ordinary temperatures, it is advantageously applicable to many industrial uses. In addition, since an epoxy resin can be cured by the cyclohexanetricarboxylic anhydride without needing a curing accelerator, it is industrially advantageous as a curing agent. Further, the color number of the cyclohexanetricarboxylic anhydride which is liquid at ordinary temperatures can be reduced by purification, it is also useful for use in optical applications.

Thus, the cyclohexanetricarboxylic anhydride which is liquid at ordinary temperatures is applicable to the uses requiring a high transparency, for example, applicable to insulating sealing materials for photoelectric transducers such as light emitting devices including LED and semiconductor lasers, photoconductive devices, photoreceptors such as photodiodes, solar cells, phototransistors and photothyristers, and optocouplers such as photocouplers and photointerrupters; adhesives for liquid crystals; photosensitive resins; surface coating agents for plastics, glass and metals; and decorative materials.

The cyclohexanetricarboxylic anhydride which is liquid at ordinary temperatures is also applicable to the curing agent for heat-curable resin compositions which are suitable for preparing coating liquids for forming protective films of color filters constituting liquid crystal displays (LCD), solid-state image sensors such as charge coupled device (CCD), or electroluminescent (EL) devices, etc.

The heat-curable resin compositions containing the cyclohexanetricarboxylic anhydride which is liquid at ordinary temperatures are further applicable to forming insulating seals and shaped articles of 2 mm thick or more by a method such as potting, casting filament-winding and lamination. Specifically, such heat-curable resin compositions are applicable to the insulating seals for heavy electric apparatuses such as mold transformers including current transformers (CT), zero layer current transformers (ZCT), potential transformers (PT) and grounding potential transformers (ZPT); parts of gas switches including insulating spacers, supporting insulators, operating rods, closed terminals, bushings, insulating pillars, etc.; parts of solid-state insulator switches; parts of automatic overhead wiring apparatuses including rotary insulators, voltage detector elements, general capacitors, etc.; parts of underground wiring apparatuses including mold disconnecting switches, power transformers, etc.; static condensers; resin insulators; and linear motor car coils, and also applicable to impregnating varnishes for coils of various rotating apparatuses such as generators and motors. In addition, the heat-curable resin composition of the present invention may also be used in weak electric applications such as potting resins for flyback transformers, ignition coils or AC capacitors; transparent sealing resins for LED, detectors, emitters or photocouplers; and impregnating resins for film capacitors and various coils.

In addition to the production of laminates, the cyclohexanetricarboxylic anhydride which is liquid at ordinary temperatures is further applicable to laminates and the uses not necessarily requiring insulating properties, for example, curing agents for heat-curable resin compositions which are used in the production of various FRP shaped articles, various coating materials, adhesives and decorative materials; raw materials and modifiers for polyimide resins, polyamideimide resins, polyamide resins, polyester resins and alkyd resins; raw materials for plasticizers and lubricating oils; intermediates for medicines and agricultural chemicals; raw materials for coating resins; and raw materials for toner resins.

The present invention will be described in detail with reference to the following examples and comparative examples. However, it should be noted that the scope of the present invention is not limited to the following examples.

In the following examples, the analysis, fractionation and identification of the products were carried out by using HPLC and NMR under the following conditions.

(1) HPLC Analysis
Apparatus: HP 1100(B) manufactured by Agilent Technologies, Inc.
Column: YMC-Pack CN 120 Å S-5 µm; 4.6 mm×150 mm
Mobile phase: n-hexane/tetrahydrofuran=90/10
Column temperature: 40° C.
Flow rate: 1.0 ml/min
Sample solution: about 7000 ppm acetonitrile solution
Injected amount: 5 µl (2) HPLC Fractionation
Apparatus: LC-6A manufactured by Shimazu Corporation
Column: CAPCELL PAK CN 120 Å 5 µm; 20 mm×250 mm
Mobile phase: n-hexane/tetrahydrofuran=95/5
Column temperature: room temperature
Flow rate: 10 ml/min
Sample solution: 8 mg/ml acetonitrile solution
Injected amount: 1 µl
Fractionation: Cut 1, Rt=from 17 to 19 min
Cut 2, Rt=from 19.5 to 24 min
Rt: retention time (3) NMR Measurement
The planar structure was determined by a two-dimensional NMR analysis. Separately, the coupling constant (J value) between protons was determined according to a decoupling method (R. M. Silverstein, B. C. Bassler, "Spectrometric Identification of Organic Compound" Tokyo Kagaku Dojin Co., Ltd.) to distinguish axial proton from equatorial proton, thereby estimating the stereostructure.
Apparatus: JNM-ALPHA-400 (400 MHz) manufactured by JEOL, Ltd.
Solvent: Cut 1: acetone-d6, DMSO-d6 (decoupling $^1$H-NMR)
Cut 2: acetone-d6
Probe: TH5 (5 mmφ)
Method: Mono-dimensional NMR for $^1$H-NMR, $^{13}$C-NMR, DEPT135, and decoupling $^1$H-NMR Two-dimensional NMR for HHCOSY, HMQC, HMBC, and NOESY

EXAMPLE 1

Into a four-necked flask equipped with a thermometer, a stirrer, a condenser and a heat controller, was charged 100 parts of 1,2,4-cyclohexanetricarboxylic acid, which was then melted under heating at 250° C. for 3 h in a nitrogen gas flow, to obtain a pale yellow, transparent, liquid 1,2,4-cyclohexanetricarboxylic acid-1,2-anhydride. The degree of anhydrization was 95% based on the starting 1,2,4-cyclohexanetricarboxylic acid, and the viscosity of the obtained liquid 1,2,4-cyclohexanetricarboxylic acid-1,2-anhydride was 14.6 Pass at 60° C.

The HPLC analysis on the obtained liquid anhydride showed two peaks (Rt=7.5 min and 8.7 min). Then, the liquid anhydride was fractionated by HPLC, to obtain Cut 1 and Cut 2 corresponding to the above two peaks. As the results of NMR measurement on each cut, Cut 1 had the planar structure of the formula 3 and identified as trans,trans-1,2,4-cyclohexanetricarboxylic acid-1,2-anhydride represented by the formula 1 (Tables 1 and 2), and Cut 2 had the planar structure of the formula 4 and identified as cis,cis-1,2,4-cyclohexanetricarboxylic acid-1,2-anhydride represented by the formula 2 (Tables 3 and 4).

The liquid anhydride contained 63.2% by mass of trans,trans-1,2,4-cyclohexanetricarboxylic acid-1,2-anhydride and 36.8% by mass of cis,cis-1,2,4-cyclohexanetricarboxylic acid-1,2-anhydride.

TABLE 1

(1)

(2)

(3)

(4)

TABLE 1

Cut 1 $^1$H-NMR

| Chemical Shifts | Signal lines | Number of $^1$H | Symbols |
|---|---|---|---|
| 10.87 | broad singlet | 1 | a |
| 3.68 | multiplet | 1 | b |
| 3.32 | multiplet | 1 | c |
| 2.48 | multiplet | 1 | d |
| 2.29 | multiplet | 1 | e |
| 2.15 | multiplet | 1 | f |
| 1.98 | multiplet | 2 | g, h |
| 1.64 | multiplet | 2 | i, j |

REF Signal 2.05 ppm: residual proton of acetone-d6

TABLE 2

Cut 1 $^{13}$C-NMR

| Chemical Shifts | Signal lines | Number of $^{13}$C | Symbols |
|---|---|---|---|
| 175.40 | singlet | 1 | A |
| 174.24 | singlet | 1 | B |
| 173.89 | singlet | 1 | C |
| 40.37 | singlet | 1 | D |
| 40.29 | singlet | 1 | E |
| 38.51 | singlet | 1 | F |
| 25.44 | singlet | 1 | G |
| 24.74 | singlet | 1 | H |
| 24.42 | singlet | 1 | I |
| REF Signal | 29.8 ppm: acetone-d6 | | |

TABLE 3

Cut 2 $^1$H-NMR

| Chemical Shifts | Signal lines | Number of $^1$H | Symbols |
|---|---|---|---|
| 10.78 | broad singlet | 1 | a |
| 3.57 | multiplet | 1 | b |
| 3.35 | multiplet | 1 | c |
| 2.46 | multiplet | 1 | d |
| 2.37 | multiplet | 1 | e |
| 2.22 | multiplet | 1 | f |
| 1.99 | multiplet | 1 | g |
| 1.85 | multiplet | 1 | h |
| 1.58 | multiplet | 1 | i |
| 1.42 | multiplet | 1 | j |
| REF Signal | 2.05 ppm: residual proton of acetone-d6 | | |

TABLE 4

Cut 2 $^{13}$C-NMR

| Chemical Shifts | Signal lines | Number of $^{13}$C | Symbols |
|---|---|---|---|
| 175.46 | singlet | 1 | A |
| 174.28 | singlet | 1 | B |
| 173.63 | singlet | 1 | C |
| 40.36 | singlet | 2 | D, E |
| 39.20 | singlet | 1 | F |
| 28.33 | singlet | 1 | G |
| 25.56 | singlet | 1 | H |
| 21.34 | singlet | 1 | I |
| REF Signal | 29.8 ppm: acetone-d6 | | |

EXAMPLE 2

By vacuum-distilling 100 parts of the pale yellow, transparent liquid 1,2,4-cyclohexanetricarboxylic acid-1,2-anhydride obtained in Example 1 under a pressure of 10 mmHg (1.3 kPa), 89 parts of colorless, transparent, liquid 1,2,4-cyclohexanetricarboxylic acid-1,2-anhydride having a degree of anhydrization of 99.8% was obtained. The color number of the obtained 1,2,4-cyclohexanetricarboxylic acid-1,2-anhydride was 45 Hazen when measured by a spectrocolorimeter JUKI JP-7100F.

COMPARATIVE EXAMPLE 1

Into a four-necked flask equipped with a thermometer, a stirrer, a condenser and a heat controller, were charged 100 parts of 1,2,4-cyclohexanetricarboxylic acid, 67 parts of acetic anhydride and 333 parts of glacial acetic acid. The contents were stirred for anhydrization at 120° C. for one hour under heating in a nitrogen gas flow. After cooling to 25° C., the precipitated crystals were separated by filtration and dried in a nitrogen gas flow to obtain a white, solid 1,2,4-cyclohexanetricarboxylic acid-1,2-anhydride.

The HPLC analysis on the obtained solid anhydride showed only one peak (Rt=8.7 min). As a result of NMR measurement, the solid anhydride was identified as cis,cis-1,2,4-cyclohexanetricarboxylic acid-1,2-anhydride represented by the formula 2. No trans,trans-1,2,4-cyclohexanetricarboxylic acid-1,2-anhydride represented by the formula 1 was detected.

EXAMPLE 3

Into a four-necked flask equipped with a thermometer, a stirrer, a condenser and a heat controller, was charged 100 parts of 1,2,4-cyclohexanetricarboxylic acid-1,2-anhydride (white solid) obtained in Comparative Example 1, which was then melted at 250° C. under heating for 3 h in a nitrogen gas flow, to obtain a pale yellow, transparent, liquid 1,2,4-cyclohexanetricarboxylic acid-1,2-anhydride.

The degree of anhydrization was 99.7% based on the starting 1,2,4-cyclohexanetricarboxylic acid, and the viscosity of the obtained liquid 1,2,4-cyclohexanetricarboxylic acid-1,2-anhydride was 14.9 Pa·s at 60° C. The obtained liquid anhydride contained 62.5% by mass of trans,trans-1,2,4-cyclohexanetricarboxylic acid-1,2-anhydride represented by the formula 1 and 37.5% by mass of cis,cis-1,2,4-cyclohexanetricarboxylic acid-1,2-anhydride represented by the formula 2.

INDUSTRIAL APPLICABILITY

According to the method of the present invention, a cyclohexanetricarboxylic anhydride which is liquid at ordinary temperatures can be easily produced from known cyclohexanetricarboxylic acids or its anhydrides. Because of the liquid nature and easiness of handling, the liquid cyclohexanetricarboxylic anhydride is advantageously applicable to various industrial uses.

The cyclohexanetricarboxylic anhydride being liquid at ordinary temperatures of the present invention is useful as coating compositions, adhesives, shaped articles, sealing resins for photosemiconductors, curing agent for heat-curable resin compositions which are suitable for preparing coating liquids for forming protective films of color filters constituting liquid crystal displays (LCD), solid-state image sensors (CCD) or electroluminescent (EL) devices, raw materials or modifiers for polyimide resins, polyamideimide resins, polyamide resins, polyester resins or alkyd resins, raw materials for plasticizers and lubricant oils, intermediates for medicines and agricultural chemicals, raw material for coating resins, raw material for toner resins, etc.

What is claimed is:

1. Trans, trans-1,2,4-cyclohexanetricarboxylic acid-1,2-anhydride represented by the following formula 1:

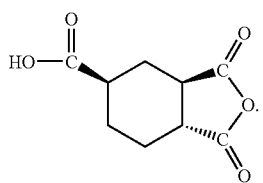
(1)

2. A cyclohexanetricarboxylic anhydride being liquid at ordinary temperatures which comprises trans, trans-1,2,4-cyclohexanetricarboxylic acid-1,2-anhydride as defined in claim 1.

3. The cyclohexanetricarboxylic anhydride being liquid at ordinary temperatures according to claim 2, which has a color number of 100 Hazen or less.

4. A method of producing the cyclohexanetricarboxylic anhydride being liquid at ordinary temperatures as defined in claim 2, which comprises a step of melting 1,2,4-cyclohexanetricarboxylic acid and/or 1,2,4-cyclohexanetricarboxylic acid-1,2-anhydride at 180 to 300° C. by heating.

5. The method according to claim 4, which further comprises a step of purifying the cyclohexanetricarboxylic anhydride by distillation after the step of melting by heating.

* * * * *